United States Patent [19]

Perouse

[11] Patent Number: 5,800,506
[45] Date of Patent: Sep. 1, 1998

[54] DEVICE FOR TREATING A BLOOD VESSEL

[75] Inventor: Eric Perouse, L'Isle Adam, France

[73] Assignee: Laboratoire Perouse Implant, Bornel, France

[21] Appl. No.: 427,904

[22] Filed: Apr. 26, 1995

[30] Foreign Application Priority Data

Apr. 26, 1994 [FR] France .................................. 94 05034

[51] Int. Cl.⁶ .................................................. A61F 2/06
[52] U.S. Cl. .................................. 623/1; 623/11; 623/12
[58] Field of Search .................................. 623/1, 11, 12, 623/13; 606/151, 108, 192–195, 198; 604/904

[56] References Cited

U.S. PATENT DOCUMENTS 4,955,859  9/1990  Zilber .
5,246,452  9/1993  Sinnott ................................... 623/1
5,267,953  12/1993  Paul et al. ............................ 604/904

FOREIGN PATENT DOCUMENTS 0 423 916  4/1991  European Pat. Off. .
2 688 688  9/1993  France .
522 204  3/1931  Germany .
2 264 236  8/1993  United Kingdom .

Primary Examiner—John G. Weiss
Assistant Examiner—Francis K. Cuddihy
Attorney, Agent, or Firm—Wenderoth, Lind & Ponack

[57] ABSTRACT

A device for treating a blood vessel comprises an outer sheath (10) containing, on the one hand, an endoprosthesis (1) whose distal end is equipped with a cord (4), and, on the other hand, a support (9). The distal end of the endoprosthesis (1) is connected to the support (9) in a separable manner by way of the cord (4). The device is used for the treatment of arterial atheroma.

15 Claims, 4 Drawing Sheets

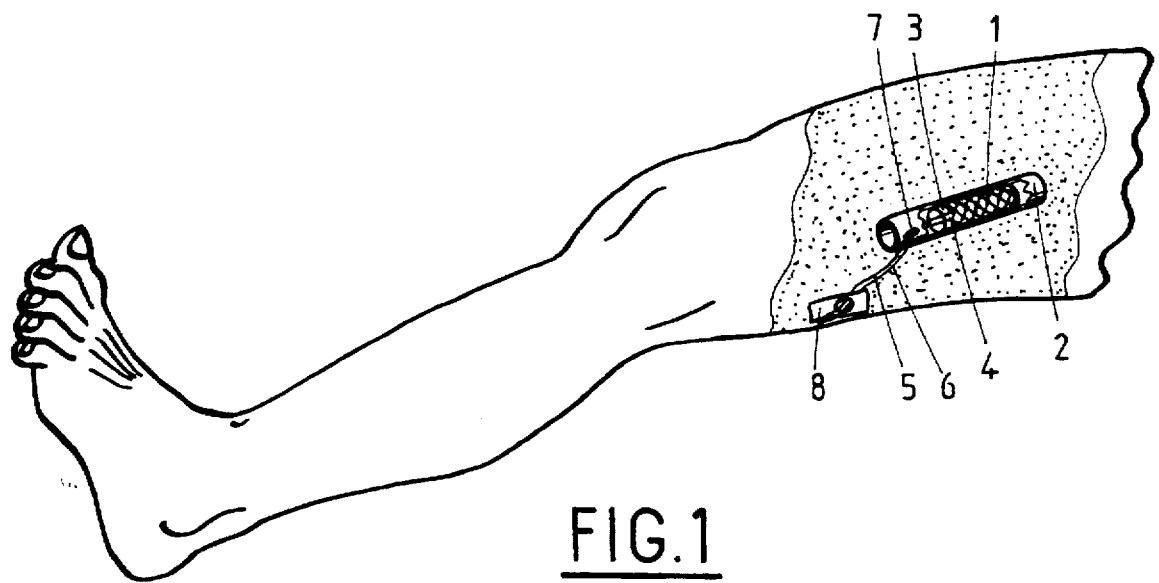
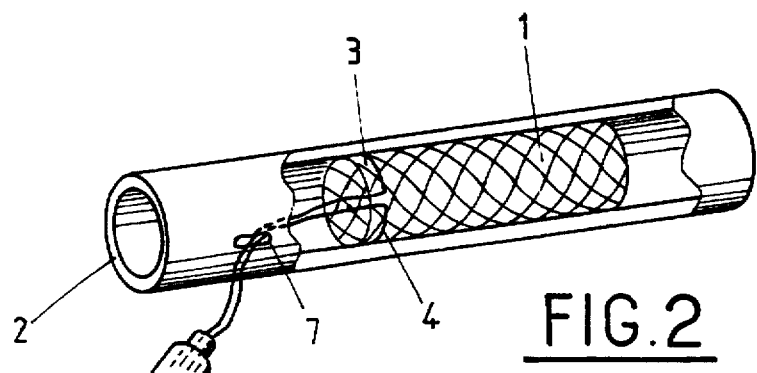
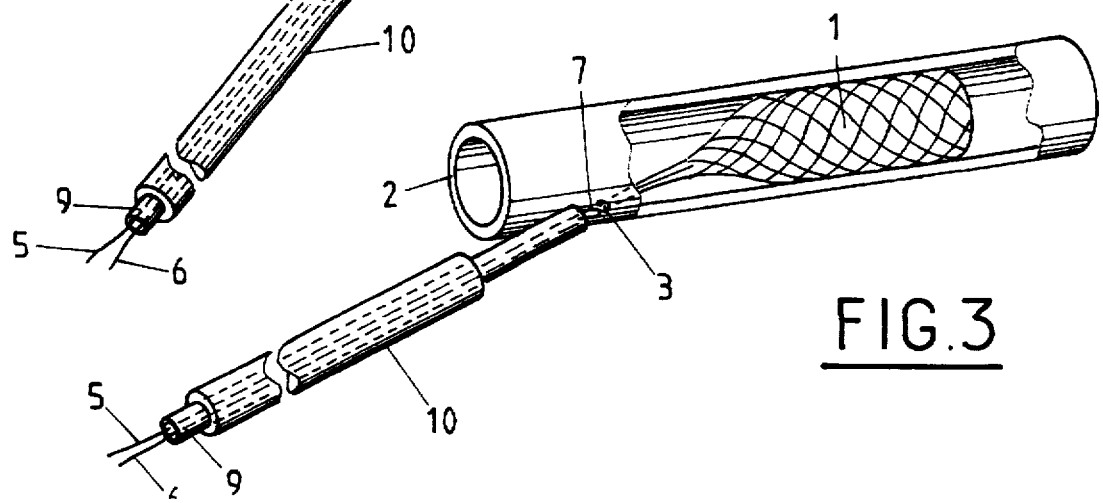

5,800,506

DEVICE FOR TREATING A BLOOD VESSEL

FIELD OF THE INVENTION

The present invention relates to a device for treating a blood vessel. The device is used in particular for supporting atheromatous arteries following dilation, or equally for bypassing aneurisms.

SUMMARY OF THE INVENTION

The object of the invention is to provide a treatment device which permits exact positioning of the endoprosthesis in an artery without risk of damaging this endoprosthesis, and which does this by simple, reliable and inexpensive means.

To this end, the invention relates to a device for treating a blood vessel, characterized in that it comprises an outer sheath containing, on the one hand, an endoprosthesis whose distal end is equipped with a cord, and, on the other hand, a support. The distal end of the endoprosthesis is connected to the support in a separable manner by way of the said cord.

The device for treating a blood vessel according to the invention can include one or more of the following characteristics:

- the support is hollow, and at least one strand of the cord extends through the support;
- the cord comprises a ligature thread forming a loop which includes two strands threaded freely about the distal end and continuing a distance from the endoprosthesis;
- the cord comprises a ligature thread forming a loop which is fixed at one point to the endoprosthesis, and including at least one strand which extends a distance from the endoprosthesis;
- the cord includes a ligature thread forming a running knot and finishing with an attachment member;
- the support bears an inflatable balloon surrounded by the endoprosthesis, the latter being of a plastically deformable type;
- the endoprosthesis is self-expanding; and
- the endoprosthesis includes, at its proximal end, a second cord forming a cord for selective contraction.

BRIEF DESCRIPTION OF THE DRAWINGS

Illustrative embodiments of the invention will now be described with reference to the attached drawings, in which:

FIG. 1 is a side view, in partial section, of an endoprosthesis implanted in a femoral artery of a leg;

FIG. 2 represents the means for recovering this endoprosthesis;

FIGS. 3 and 4 illustrate the stages in the recovery of the implanted endoprosthesis;

DETAILED DESCRIPTION OF THE PREFERRED EMBODIMENTS

Figure 4:
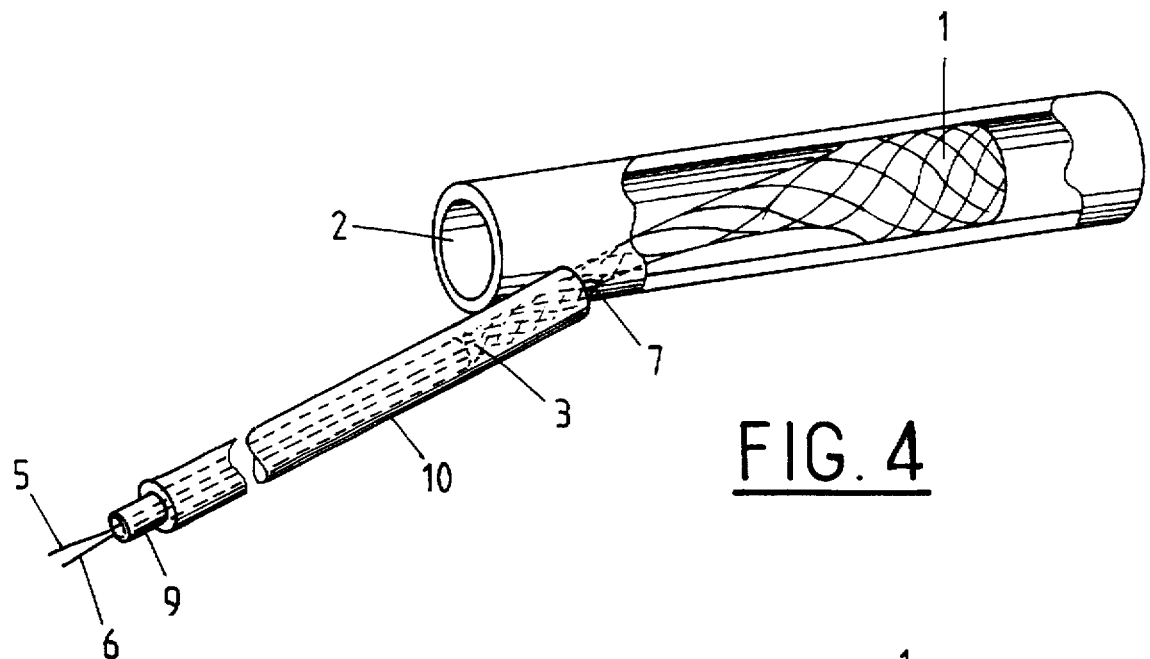

FIG. 1 shows a tubular endoprosthesis 1 implanted in the femoral artery 2 of a patient. This endoprosthesis is essentially of a known type, described in French patent application FR-A-2,688,401. This endoprosthesis 1 consists of a tubular lattice embedded in a film. The lattice consists of stainless steel of biocompatible quality. The film is made of a material which is extensible and impervious to liquids, such as an elastomer. The endoprosthesis 1 is, for example, made self-expanding by using a stainless steel which has properties of resiliency.

The self-expanding endoprosthesis 1 can be put into position using an appropriate positioning instrument, for example the one described in the French patent application FR-A-2,688,688, in which the endoprosthesis is compressed radially in a tulip-shaped end of the instrument. The petals of the tulip are opened out in situ in order to free the endoprosthesis.

FIG. 1 of the present application shows that one of the ends 3 of the tubular endoprosthesis 1 bears, around its circumference, a ligature thread 4 whose two strands 5 and 6 pass through the wall of the artery 2 via an opening 7, then pass through the skin in order to be taken up and fixed to the surface of the skin of the patient by a bandage 8.

The ligature thread 4 is threaded and interlaced freely, that is to say with the possibility of sliding, in the meshes of the end 3 of the endoprosthesis 1, as is shown in FIG. 2. Its two strands emerge therefrom alongside one another, through the same mesh of the lattice and in the vicinity of the proximal intersection of this mesh.

The recovery of the endoprosthesis 1 will now be described with reference to FIGS. 2 to 4.

FIG. 2 shows that, in order to recover the endoprosthesis, the strands 5 and 6 of thread are unwound and are passed through a catheter or support 9, itself engaged in a sheath 10 of smaller length. In a first stage, this catheter 9 and this sheath 10 are located outside the patient.

The catheter 9 is then slid over the strands 5 and 6 (FIG. 3), and it passes through the skin and the artery of the patient until it reaches the end 3 of the endoprosthesis. The strands 5 and 6 are then drawn tight by the operator, which results in a contraction of this end 3. By keeping the strands 5 and 6 fixed tight and keeping the catheter 9 stationary, the operator slides the sheath 10 up to the contracted end of the endoprosthesis, via the opening 7. The distal end of the sheath 10 then advances over the proximal end 3 of the endoprosthesis (FIG. 4), which remains stationary in the artery throughout the operation. The sheath then penetrates inside the artery 2 until it envelops or "swallows" the endoprosthesis 1 over its entire length. The latter is thus completely separated from the wall of the artery.

The combination of taut strands, catheter, and sheath enveloping the radially compressed endoprosthesis, can then be gently removed from the patient; the endoprosthesis 1 is thus recovered.

Alternatively, the thread 4 could be fixed via one end to the proximal end of the endoprosthesis, encircle the latter by interlacing in the lattice, and continue freely in a single strand.

Figure 5:
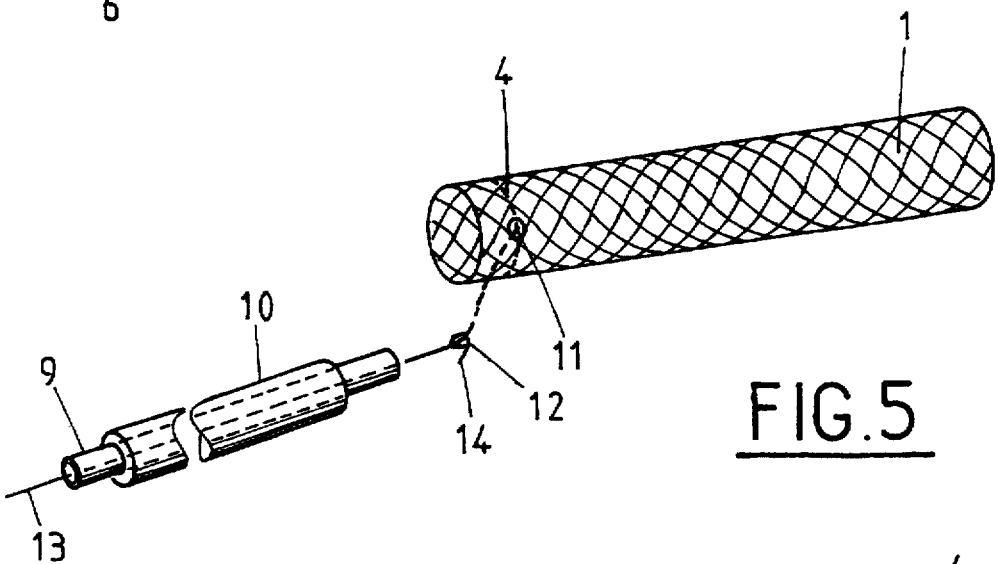
FIG. 5 shows a variant of the endoprosthesis in FIG. 1.

FIG. 5 illustrates a variant of the attachment device. The ligature thread 4 encircles the proximal end of the endoprosthesis 1, one of its ends forming an eyelet of a running knot 11 through which there passes the other end of the thread, which bears an attachment ring 12. When it is desired to compress this end, it suffices, by angioscopy, to attach to the ring 12 an auxiliary thread 13 which is provided at its distal end with a hook 14, and on which the catheter 9 is subsequently passed, as has already been described. The endoprosthesis is then recovered in the same way as before, by means of the catheter 9 and the sheath 10.

Figure 6:
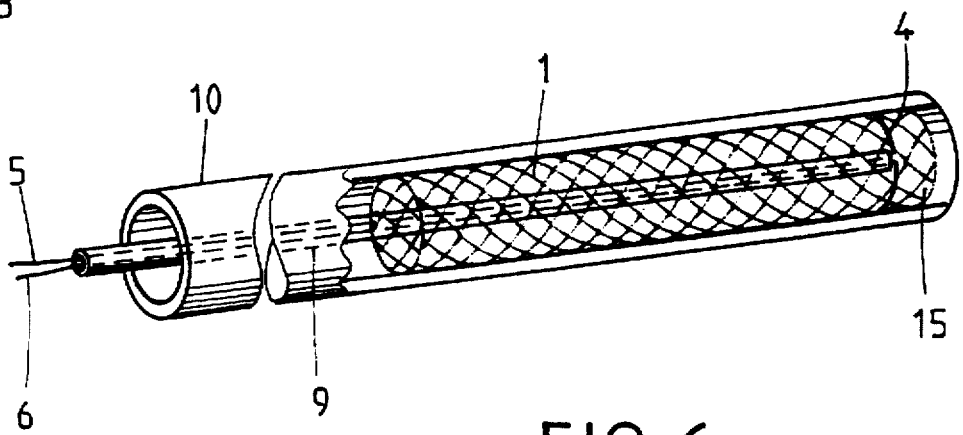
FIG. 6 is a side view of a device for treating a blood vessel, according to the invention, by positioning of an endoprosthesis.

The positioning of the self-expanding endoprosthesis 1 in the artery 2 is carried out, according to the invention, by the device illustrated in FIG. 6. The endoprosthesis 1 is now equipped, at its distal end 15, with the ligature thread 4 which is passed through the meshes of the circumference, finishing with strands 5 and 6, in the same way as in FIG. 2.

The treatment device comprises the same elements as above, namely a catheter 9 and a sheath 10. The strands 5 and 6 are passed inside the catheter 9, which forms a support and is itself arranged inside the endoprosthesis 1 over the entire length thereof. The combination of compressed endoprosthesis and catheter is inserted into the sheath 10.

Figure 7:
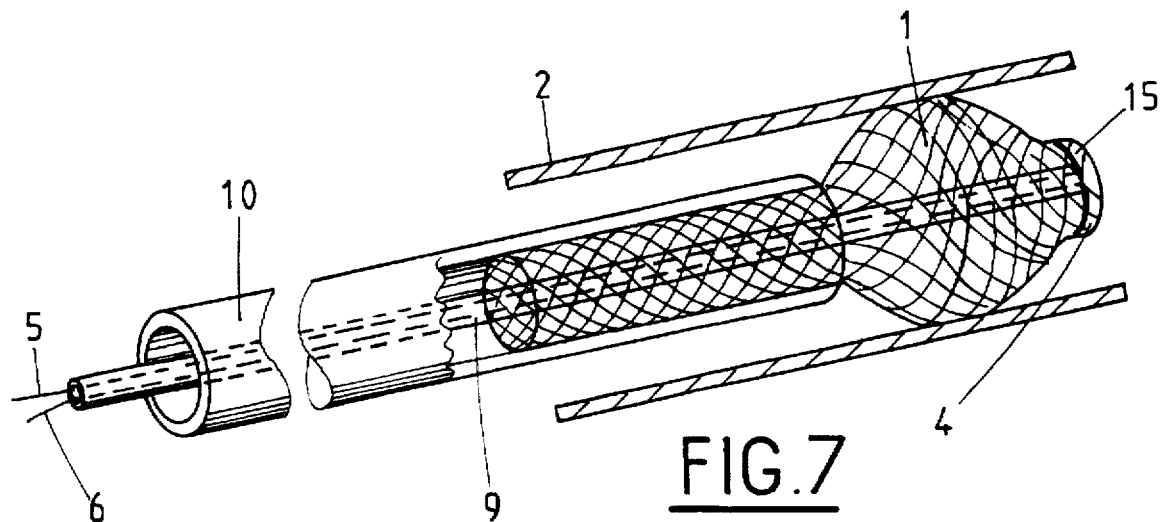
FIGS. 7 to 9 illustrate the steps in the positioning of the endoprosthesis in FIG. 6.
Figure 8:
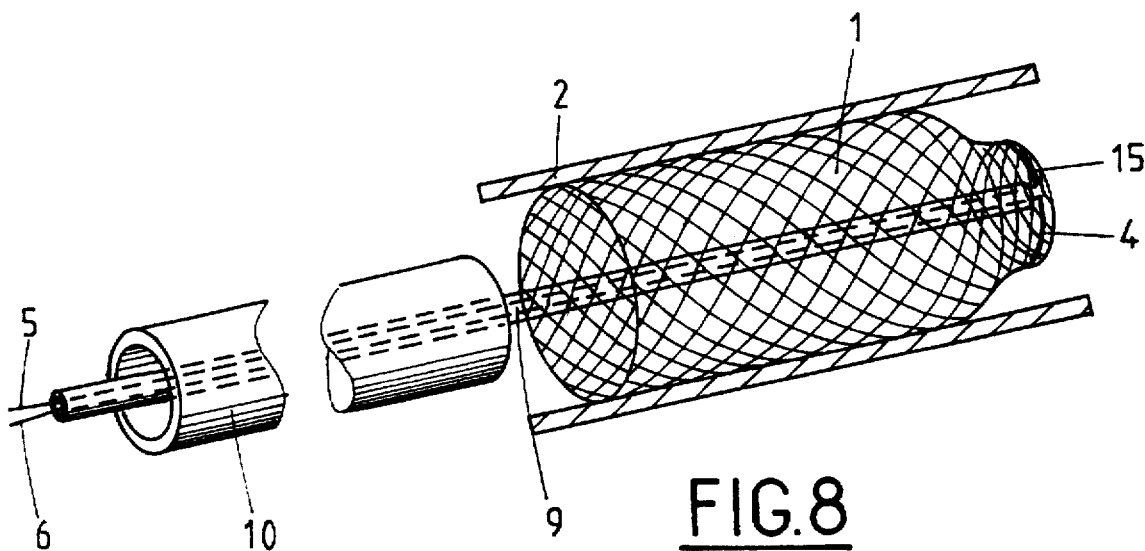
Figure 9:
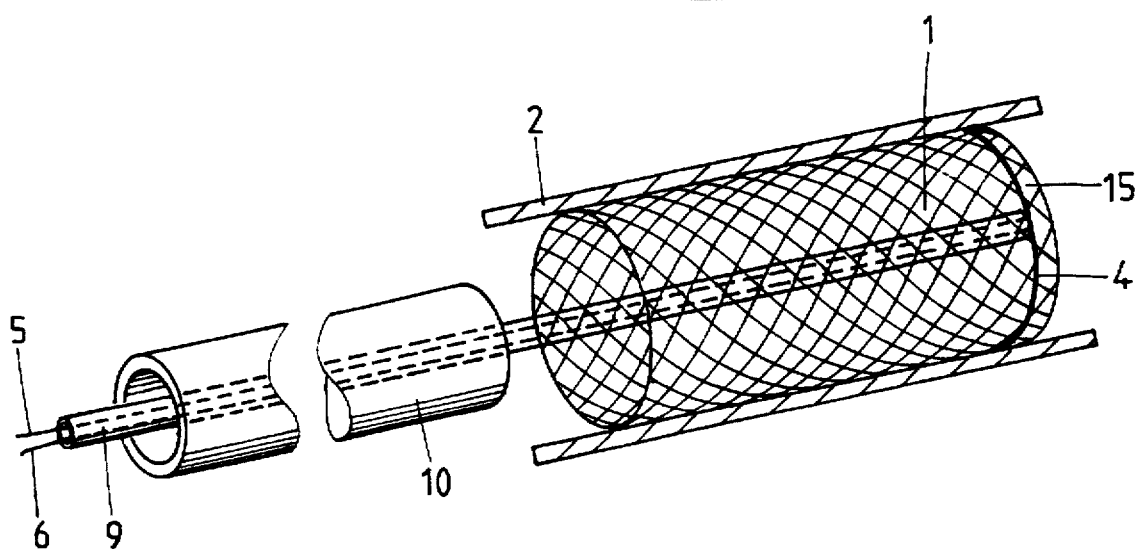

In order to facilitate the penetration of this device as far as the artery, a filiform guide can extend from outside the patient to the site of the artery where the endoprosthesis 1 is to be positioned. When the endoprosthesis is correctly positioned, the catheter is held in place and the strands 5, 6 are slightly tightened, while the sheath 10 is made to slide towards the rear, as is shown in FIGS. 7 to 9. During this operation, the endoprosthesis is held stationary via its distal end 15 by the catheter 9 and the strands 5, 6, and its part situated between the thread 4 and the distal end of the sheath 10 expands and is applied against the wall of the artery.

When the endoprosthesis has been freed completely from the sheath, the strands 5 and 6 are relaxed (FIG. 9). The operator pulls on one of the two strands in order completely to withdraw the thread 4 from the patient, and the catheter and the sheath are also removed. The endoprosthesis is then in position in the artery 2.

Figure 10:
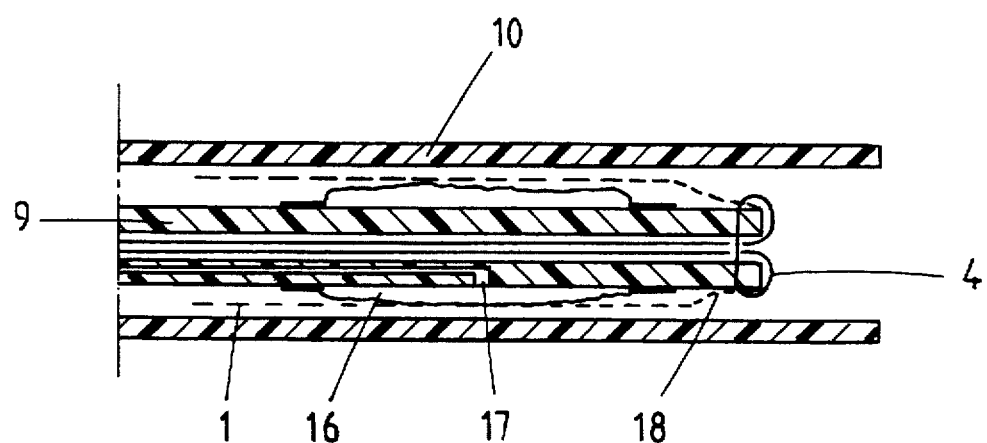
FIG. 10 is a side view of a device for treatment by positioning of another endoprosthesis a variant according to the invention.

In the case where the endoprosthesis 1 is not self-expanding, but is instead made from a lattice of plastically deformable material, its expansion is provided for by a balloon. The treatment device of such an endoprosthesis can consist (FIG. 10) of a sheath 10 enveloping a catheter 9 on which a radially expanding balloon 16 is fixed via its two ends. A channel 17 which is provided in the wall of the catheter, for delivery of expansion fluid, opens radially outwards between the two ends of the balloon 16. The endoprosthesis 1, in its radially retracted state, is arranged over the balloon 16, between the catheter 9 and the sheath 10. The distal end 18 of the endoprosthesis 1 is fixed to the distal end of the catheter 9 by the thread 4, which forms, as before, a loop which is interlaced in the lattice of the endoprosthesis and extending over the circumference thereof, and the two strands 5 and 6 of which are passed towards the rear in the catheter.

When this device has been introduced as far as the desired site, the sheath is withdrawn, while holding the catheter stationary. The strands 5 and 6 are slackened, then the balloon 16 is inflated in order to dilate the endoprosthesis 1, made of malleable metal, and is then deflated. The catheter 9 is then removed gently, leaving the endoprosthesis in place, and the thread 4 is finally withdrawn by pulling on one of the two strands 5 and 6.

As will be understood, the endoprosthesis can be equipped with a thread 4 at each end, in order to make it possible to put it into position without pushing on its proximal end, and also to recover it easily.

Finally, the device according to the invention has the advantage of making it possible to correct an error in the positioning of the endoprosthesis in the vessel, by contracting it once more, with the aid of the thread, in order to move it to the desired site.

I claim:

1. A device for treating a blood vessel, comprising:
   an outer sheath capable of being inserted into a blood vessel;
   a vascular endoprosthesis capable of being inserted into and supporting a blood vessel and contained within said outer sheath, said endoprosthesis having a distal end;
   a support contained within said outer sheath, said support having a distal end; and
   a cord on said distal end of said endoprosthesis connecting said distal end of said endoprosthesis to said distal end of said support in a separable manner.

2. The device of claim 1, wherein said support is hollow and said cord comprises at least one strand extending through said support.

3. The device of claim 2, wherein said cord comprises a ligature thread that forms a loop which includes two strands that are threaded about said distal end so as to be freely slidable relative thereto and that extend away from said endoprosthesis.

4. The device of claim 2, wherein said cord comprises a ligature thread that forms a loop which is fixed at one point to said endoprosthesis and that comprises at least one strand that extends away from said endoprosthesis.

5. The device of claim 2, wherein said cord comprises a ligature thread that forms a running knot and an attachment member.

6. The device of claim 1, wherein said cord comprises a ligature thread that forms a loop which includes two strands that are threaded about said distal end so as to be freely slidable relative thereto and that extend away from said endoprosthesis.

7. The device of claim 1, wherein said cord comprises a ligature thread that forms a loop which is fixed at one point to said endoprosthesis and that comprises at least one strand that extends away from said endoprosthesis.

8. The device of claim 1, wherein said cord comprises a ligature thread that forms a running knot and an attachment member.

9. A device for treating a blood vessel, comprising:
   an outer sheath;
   an endonrosthesis contained within said outer sheath, said endoprosthesis having a distal end;
   a support contained within said outer sheath; and
   a cord on said distal end of said endonprosthesis connecting said distal end of said endoprosthesis to said support in a separable manners;
   wherein said support has a inflatable balloon thereon that is surrounded by said endoprosthesis, said endoprosthesis being plastically deformable.

10. The device of claim 1, wherein said endoprosthesis is self-expanding.

11. A device for treating a blood vessel, comprising:
   an outer sheath;
   an endoprosthesis contained within said outer sheath, said endoprosthesis having a distal end;
   support contained within said outer sheath; and
   a cord on said distal end of said endoprosthesis connecting said distal end of said endoprosthesis to said support in a separable manner;
   wherein said endoprosthesis comprises, at a proximal end opposite to said distal end, a second cord that forms a cord for selective contraction of said endoprosthesis.

12. A device for treating a blood vessel, comprising:
   an outer sheath having a distal end;

a support having a distal end extending into said outer sheath;

an expandable endoprosthesis surrounding said support and located inside said outer sheath, said endoprosthesis having a distal end; and a connector on said distal end of said endoprosthesis separably connecting said distal end of said endoprosthesis with said distal end of said support.

13. The device of claim 12, wherein said connector defines a means for holding said endoprosthesis in position relative to said support upon retraction of said distal end of said outer sheath relative to said distal end of said support.

14. The device of claim 12, wherein said connector comprises a ligature thread engaged with said distal end of said endoprosthesis.

15. The device of claim 14, wherein said ligature thread extends through said support from said distal end of said endoprosthesis, into said distal end of said support and to a proximal end of said support.

* * * * *